United States Patent [19]
Lane, Jr. et al.

[11] Patent Number: 4,882,928

[45] Date of Patent: Nov. 28, 1989

[54] REFRIGERATION EFFICIENCY MONITORING SYSTEM

[76] Inventors: William E. Lane, Jr., 2539 NE. 32nd Pl., Ocala, Fla. 32570; Clayton E. Leist, II, 4010 SE. 23rd Ave., Ocala, Fla. 32671; Bradley L. Busch, 810 SW. 23rd Pl., Ocala, Fla. 32674

[21] Appl. No.: 255,880

[22] Filed: Oct. 11, 1988

Related U.S. Application Data

[63] Continuation-in-part of Ser. No. 136,550, Dec. 22, 1987, abandoned, which is a continuation-in-part of Ser. No. 919,787, Oct. 16, 1986, abandoned.

[51] Int. Cl.$^4$ ............................................. G01N 29/02
[52] U.S. Cl. ...................................... 73/19; 73/61 R; 62/129; 340/632
[58] Field of Search .................. 73/19, 61 R, 592, 599, 73/600, 602, 865.5; 340/632; 62/129

[56] References Cited

U.S. PATENT DOCUMENTS

| | | | |
|---|---|---|---|
| 3,283,562 | 11/1966 | Heisig et al. | 73/19 |
| 3,921,622 | 11/1975 | Cole | 73/61 R |
| 3,974,681 | 8/1976 | Namery | 73/61 R |
| 4,341,116 | 7/1982 | Bilstad et al. | 73/19 |
| 4,607,520 | 8/1986 | Dam | 73/19 |
| 4,644,755 | 2/1987 | Esslinger et al. | 62/129 |
| 4,763,525 | 8/1988 | Cobb | 73/61 R |

FOREIGN PATENT DOCUMENTS

| | | | |
|---|---|---|---|
| 0838552 | 6/1981 | U.S.S.R. | 73/19 |
| 1322163 | 7/1973 | United Kingdom | 73/61 R |

OTHER PUBLICATIONS

Taub, H. et al., "Principles of Communication Systems", (1971), pp. 86–91.

Electronic Sightglass TIF4000, TIF Instruments Inc., 9101 NW 7th Ave., Miami, FL 33150.
Guardsman TM Refrigerant Leak Detection System (1987), Esswood Corporation, Suite 480, 11300 Cornell Park Drive, Cincinnati, Ohio 45242.

*Primary Examiner*—John Chapman
*Assistant Examiner*—Lawrence Fess

[57] ABSTRACT

The disclosure is directed to a device for monitoring the thermodynamic state of a fluid flowing through a conduit. The device generally comprises a first electromechanical transducer acoustically coupled to the conduit, electronic drive means connected to the first electromechanical transducer to provide a driving electrical signal to the first electromechanical transducer whereby the first electromechanical transducer is oscillated to generate mechanical wave energy for transmission through the fluid flow, and a second electromechanical transducer acoustically coupled to the conduit and arranged in a spaced, acoustically coupled relation to the first electromechanical transducer to receive the mechanical wave energy transmitted through the fluid flow and conduit by the first electromechanical transducer and to convert the received mechanical wave energy into an electrical signal. The electric signal is integrated and conducted to an electronic device which is operable to detect changes in the electrical signal caused by a change in the thermodynamic state of the flowing fluid, to verify the time duration of detected changes in the electrical signal, to record events of detected changes having a time duration of more than a predetermined amount and to sound an alarm when the number of events recorded exceeds a predetermined number. The electronic device is also operatable to sound an alarm when any detected change in the thermodynamic state of the flowing fluid exceeds 30 minutes.

20 Claims, 4 Drawing Sheets

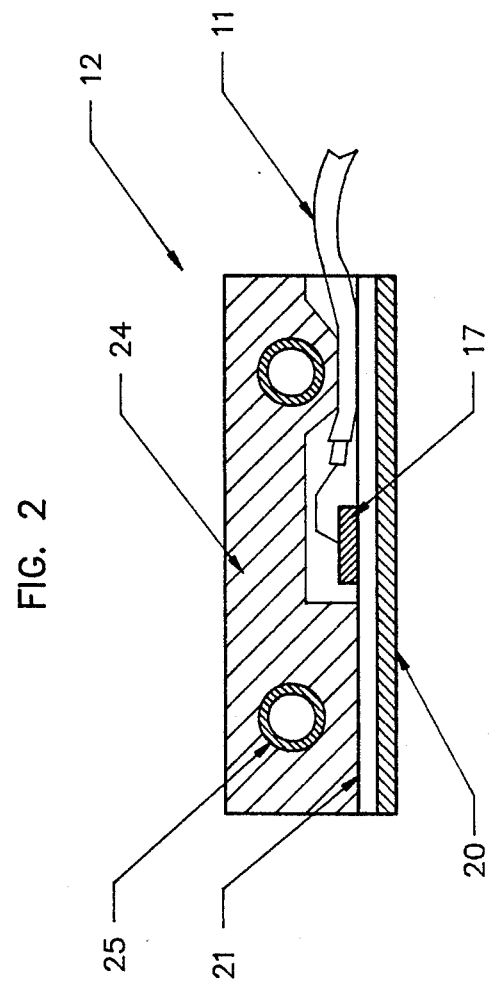
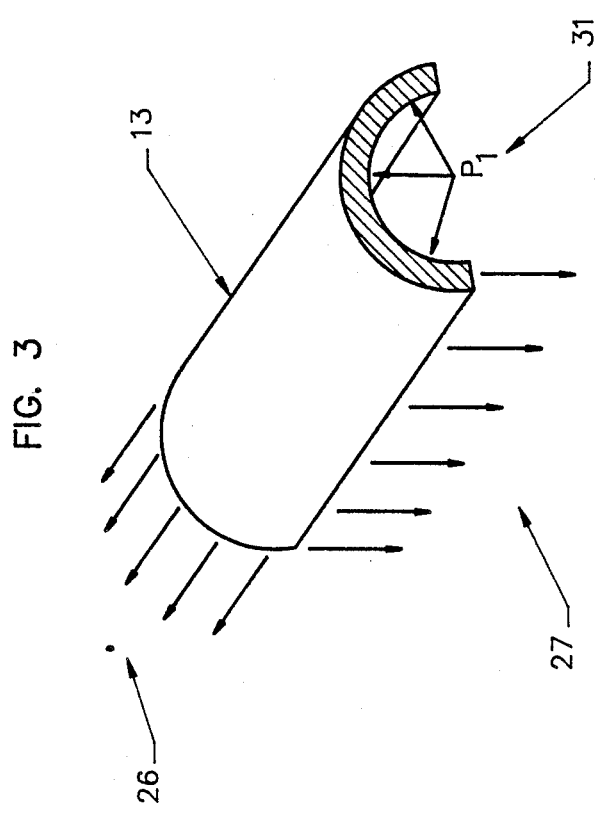

REFRIGERATION EFFICIENCY MONITORING SYSTEM

RELATED APPLICATIONS

This application is a continuation-in-part of prior application Ser. No. 136,550 now abandoned; filed Dec. 22, 1987; which prior application was a continuation-in-part of parent application Ser. No. 919,787; filed Oct. 16, 1986, now abandoned.

BACKGROUND OF THE INVENTION

The present invention is directed to a device for monitoring fluid flow in a conduit and, more particularly, to a device operable to detect inhomogeneities, such as gas bubbles, in liquid-filled pipes, to verify and record events of inhomogeneity and to activate an alarm and/or alarms under certain conditions and/or numbers of events of inhomogeneity.

In many industrial processes involving liquid flow, it is often highly important that the fluid flow be maintained at a certain predetermined homogeneous flow rate. For example, in refrigeration systems or other fluid heat transfer processes, gas bubbles in the fluid input line may result in an insufficient amount of refrigerant causing a less than adequate heat transfer or inefficiency in the operation of the system. A heat transfer deterioration is highly undesirable in that the system may ultimately be unable to maintain the storage temperature required for the products stored in the refrigeration system. Thus, it is an advantage to provide a means in the system whereby an operator may determine that the flow input is homogeneous and completely fills the volume of the input line.

Within the closed system of a refrigeration system, the thermodynamic equilibrium of the fluorocarbon coolant is constantly changing between the liquid and gaseous phase as the result of the variations in temperature and pressure that occur as the coolant circulates between the compressor and the evaporator.

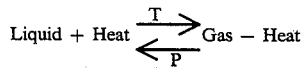

The coolant is usually in the liquid state under high pressure at the inlet conduit as it leaves the condenser and in the gaseous state under low pressure as it leaves the evaporator. However, under normal operation frequent frothing and surging does occur due to the rapid passage of gas bubbles. The presence of this frothing (Flash Gas) at the inlet conduit is caused by the pressure changes downstream during the defrost cycle and as one or more evaporators cycle on and off.

An advantage of the device to be described is that it will detect such thermodynamic changes, analyze the data and alert the operator within about 30 minutes if there is a leak or other malfunction that will ultimately result in an unsatisfactory storage temperature.

An important advantage of the present invention is that it can be used to monitor the flow and thermodynamic state of all known commercial refrigerants although the physical properties of such refrigerants vary widely.

Another advantage of the present invention in monitoring refrigeration systems or other fluid transfer processes is the early detection of leaks in the system or other abnormalities such as malfunctioning of the compressor or valves which malfunction would cause a change in the thermodynamic state of the coolant as it flows through the system. An obstruction in the drier filter would also be detected by the monitor of the present invention at an early stage.

The monitor to be described has particular application to large multiple (parallel) refrigeration units of up to 240 horse power that are found in large supermarkets. A small leak, if not detected early, can result in the release of large amounts (hundreds of pounds) of chlorofluorocarbons into the atmosphere.

The present invention will also have a favorable environmental impact. In 1974, Sherwood Rowland and Mario Molina of the Irving Campus of the University of California, first warned that chloroflorocarbons might seriously damage the ozone layer in the stratosphere. In 1985 a team of British scientists announced the disconcerting news that the springtime ozone had diminished to nearly half of what they had measured a few years before. Two-thirds of the springtime ozone over Antarctica is now missing. There is a hole in the Antarctic ozone layer. It has shown up every spring since the late 1970's. While it heals itself in winter, the hole seems to last longer each spring.

Concern that a depletion of the ozone layer will increase the incidence of skin cancer and eye cataracts among the world population is such that the United States along with Canada and Scandanavian countries voluntarily ended the use of chlorofluorocarbons in aerosol sprays during the 1970's. In September of 1987, many of the nations that use and produce chlorofluorocarbons met in Montreal to consider the possibility of an agreement to limit chlorofluorocarbon use. Now 37 nations including the USSR have agreed to a schedule of cutbacks in chlorofluorocarbon production, so that by 1989 production reverts to 1986 levels, and by 1999 to about 50 percent of that.

An early prior art proposal for the detection of gas bubbles in a refrigeration system inlet line comprises a sight glass to enable visual observation of the fluid flow. This approach has significant drawbacks in that it requires constant observation by an operator. Indeed, comprehensive monitoring of the system through the use of a sight glass is impractical since it is not economically feasible to maintain constant, round-the-clock surveillance by a human operator. The sight glass, at most, enables a spot check on the system to perhaps verify other indications of refrigerant insufficiency. Moreover, the use of a sight glass may not be feasible in certain applications such as refrigeration systems mounted on motor vehicles and in home air conditioners.

A second, more sophisticated proposal, utilizes wave energy transmissions such as ultrasonic sound waves which are transmitted through the fluid flow as a means to detect impurities, e.g., gas bubbles in a liquid refrigerant. An example of a device based upon the wave energy transmission approach is disclosed in U.S. Pat. Nos. 4,235,095 and 4,138,879. The prior device includes a pair of electromechanical transducers which are mounted upon the refrigerant inlet line in an acoustically coupled relationship. One of the transducers is operated to transmit ultrasonic sound waves through the inlet line. The other transducer is utilized to receive the transmitted ultrasonic sound waves and to convert the received waves into a electrical signal.

In accordance with the theory of operation of the disclosed device, the sound conductivity of the fluid flow within the input line will be a function of the material content of the line. Under normal operating conditions, the fluid line will contain only the refrigerant and transmit the sound waves according to the refrigerants's inherent sound conductivity properties. When impurities such as gas bubbles flow through the line, the conductivity of the fluid flow will be altered by the presence of gas pockets within the inlet line thereby varying the intensity of the ultrasonic sound waves received by the receiving transducer. This, in turn, will vary the electrical signal produced by the receiving transducer to indicate impurities in the inlet line.

Thus, the prior art proposal does provide a device for the detection of gas bubbles in a refrigerant but operates in a different manner (the driving signal to the transmitting transducer is increased as gas bubbles pass this transducer. Moreover, the apparatus described in U.S. Pat. Nos. 4,235,095 and 4,138,897 require temperature sensors at the input and output of the evaporator and a differential temperature indicating circuit to interpret the output of the device described and claimed.

Another shortcoming of the heretofore known wave transmission devices is that the impurity detection merely indicates the presence of impurities, such as gas bubbles, at the instances of occurrence and does not provide information critical to the comprehensive monitoring of the refrigeration system over time. The operation of devices known prior to our invention might notify an operator of the flow of gas bubbles through the inlet line but does not give any indication as to whether the gas flow is a momentary and not untypical abberation in refrigerant flow or a significant event of refrigerant insufficiency adversely effecting efficient operation of the system.

It is a primary objective of the invention to provide a wave transmission type impurity indicator which not only detects and indicates the presence of impurities in the fluid flow, but also verifies the occurrence of significant events of inhomogeneity in fluid flow, records the number of significant events within a predetermined period of operation of the system and compares the number of recorded events to a predetermined acceptable maximum number of events.

Another object of this invention is to notify the operator of a single significant event, the duration of which exceeds 30 minutes.

SUMMARY OF THE INVENTION

Generally, the device of this invention comprises a pair of electromechanical Transducers mounted to the inlet line of a fluid flow system such as a refrigeration system in an acoustically coupled relation. One of the Transducers is driven by a driving amplifier to continuously transmit ultrasonic sound waves through the inlet line. The other Transducer is arranged to receive the transmitted sound waves and to convert the received waves into an electrical signal.

The intensity of the received sound waves will be a function of the sound conductivity between the transmitting and receiving transducers. As explained above, the conductance of the ultrasonic waves through the wall of the conduit, and therefore the signal received by the receiving transducer is dependent upon the thermodynamic state of the refrigerant which will vary as indicated with temperature and pressure. The electrical signal generated by the receiving transducer is filtered, amplified and conducted to a Comparator Circuit which compares the signal to a reference signal calibrated to the normal, all refrigerant flow condition. Any deviation between the generated signal (which changes with the sound conductivity of that section of the input line that is between the two transducers) and the reference signal will activate the Comparator Circuit.

A most important aspect of the present invention, a Time Lag Integrator is employed to average the input signal to the comparator circuit, filter out anomalous glitches and thereby eliminate false indications of gas bubbles in the line. Assuming a true presence of gas bubbles, the comparator will activate a Flash Gas Indicator Circuit and an Event Timer Circuit. The flash-gas indicator circuit will indicate the presence of gas bubbles in the input line (flashing) at that instant of time; and is turned off when the averaged input signal returns to normal. The event timing cycle of the event timing circuit can be predetermined and set, e.g., 1-4 minutes, depending upon the characteristics of the refrigeration system being monitored. A continuous flow of gas bubbles through the inlet line or the predetermined amount of time set for that particular refrigeration system indicates a significant event of inhomogeneity within the inlet line and the possibility of a condition of refrigerant insufficiency. If the event timer times out while the gas bubble detection continues, a significant event is verified and a recorder circuit will be activated by the event timer circuit to count the event. If there are no gas bubbles at the inlet line (the flashing indicator is not illuminated) the event timer will not time out and the recorder circuit is not activated to count a significant event. A Reset Timer is utilized to reset the event counter circuit at periodic intervals and the event counter circuit will operate to activate and latch an Alarm and a Cycle Indicator should a predetermined number of events occur within that interval of time. The event timer circuit has a second output to a Duration Timer that will time out at the end of 30 minutes. Should the output signal from the integrator be at a level indicating inhomogeneity within the inlet line last for that period of time, the duration timer circuit will activate an alarm and a Service Indicator.

The present invention therefore provides an important improvement over the prior art that can be incorporated into automatic monitoring of refrigeration systems without penetrating the conduit. Novel circuitry is coupled with an advantageous wave transmission detection mechanism to automatically detect, verify and record critical information relating to the proper operation of a refrigeration system. The refrigeration system is continuously monitored and the operator is conveniently appraised of a flow of impurities, a verification of significant time duration of impurity flow and an indication of an unacceptable number of repeated events of significant duration within a set period of system operation. Thus, the invention affords a comprehensive overview of system operation to enable prompt and accurate detection of system malfunction and effective and efficient maintenance and repair.

For a better understanding of the above and other features and advantages of the invention, reference should be made to the following detailed description of a preferred embodiment of the invention and to the accompanying drawings.

BRIEF DESCRIPTION OF THE DRAWINGS

FIG. 2 is a sectional view of the transducer 12 illustrated in FIG. 1.

FIG. 3 illustrates the stresses that exist within the walls of the inlet line.

DETAILED DESCRIPTION OF A PREFERRED EMBODIMENT OF THE INVENTION

Figure 1:
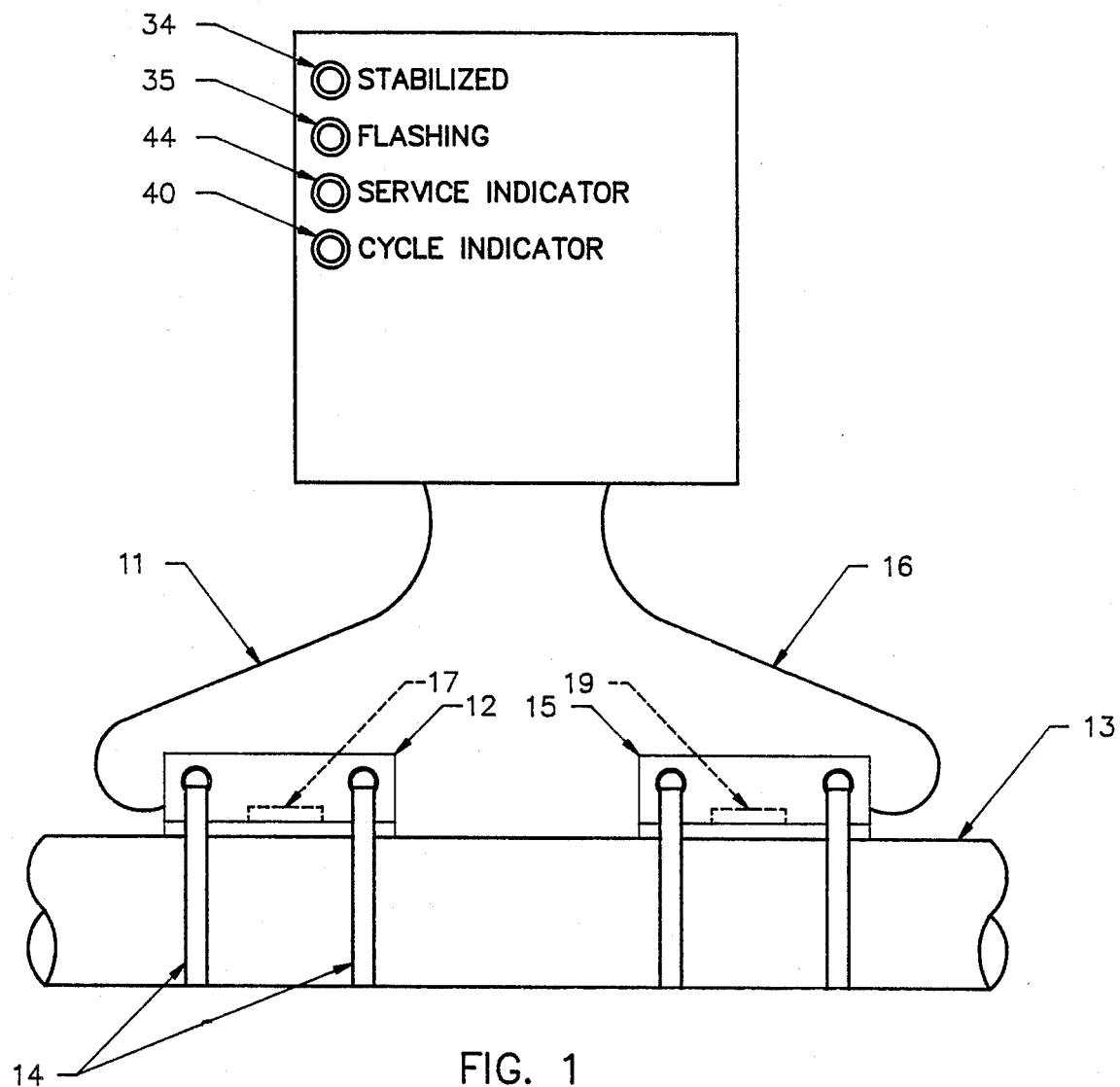
FIG. 1 is a view of the monitor showing the transducers coupled to the inlet line of a refrigeration system.

Referring now to the drawings, and initially to FIG. 1, a fluid flow monitoring device is generally indicated by the reference numeral 10. The device contains novel electronic circuitry, as will be described below, operable to generate a 44 kHz electrical signal which is transmitted through conductor 11 to a first piezo electric crystal 17 of transducer 12. The electromechanical transducer 12 is mounted upon the refrigerant inlet line 13 on the high pressure side of a refrigeration system (not specifically illustrated) by the securing straps 14 and will be oscillated by the 44 kHz signal conducted by conductor 11 to generate ultrasonic waves.

Laterally placed from the transducer 12 is a second electromechanical transducer 15. The piezo electric crystal 19 of transducer 15 converts the 44 kHz ultrasonic energy transmitted by transducer 12 through and along conduit 13 into a 44 kHz output through the conductor 16.

FIG. 2 illustrates additional details of the first electromechanical transducer 12. This transducer is coupled to the inlet line of the refrigerator system by a formed piece of synthetic or natural rubber 20 which extends along the vibrating plane 21 of the transducer 12. The piezo electric crystal is sealed from the environment by a plastic potting compound 24 formed to the housing 12 of FIG. 1 and is secured by straps that pass through the securing rings 25. This configuration has advantages over prior transducer coupling methods in that deformation of the conduit containing the fluid medium is not necessary, nor is it necessary to use silicon coupling compounds between the transducers and the conduit.

The generated 44 kHz electrical energy is transmitted via conductor 11 to the piezo electric crystal element 17 which is coupled to the vibrating plane 21. As shown in FIG. 1, the ultrasonic energy put out by the crystal is transferred along and through conduit 13 containing the refrigerant medium, and is detected by a second electromechanical transducer 15 similar to the first electromechanical transducer described above.

The second electromechanical transducer may be coupled to the inlet line at any location, preferably within 16 inches of the first electromechanical transducer. The second electromechanical transducer 15 converts the received mechanical ultrasonic energy into an electric signal, which is transmitted via conductor 16 to an amplifier within the monitoring device.

In accordance with known phenomena, the intensity of the ultrasonic waves received by the transducer 15 will be a function of the sound conductivity of that portion of the inlet line that extends between transducer 12 and transducer 15. The output signal from transducer 15 therefore is dependent upon the conductance of sound in the material of which the conduit is made, the type of refrigerant flowing through the conduit 13 and its thermodynamic state of equilibrium (pressure and gas-flashing within the conduit).

FIG. 3 depicts the pressures and stresses existing within the conduit 13. Under a pressure $P_1$ on conduit 13, both longitudinal stresses 26 and circumferential stresses 27 will exist in the conduit wall. Stresses 26 and 27 are proportional to the pressure $P_1$ which will vary widely with the temperature of the condensate and the type of refrigerant employed. Thus a factor such as a pressure drop, which reduces the effective latent heat and effective refrigeration capacity of a refrigeration system will:

1. decrease the stresses existing in the walls of the conduit, resulting in a decrease in the component of ultrasonic energy being transmitted through the conduit wall, and 2. cause flash-gas which will decrease the component of ultrasonic energy being transferred through the fluid coolant as it flows through the conduit.

We have found that the relative placement of transducers 12 and 15 is not critical to the proper operation of our device. A reference electrical signal to the transmitting transducer 12 may be easily calibrated to match an amplified output signal generated by the receiver transducer 15 during normal operation of the system, i.e., when the conduit 13 is completely filled with a homogeneous refrigerant flow. The original installation when the monitor is first installed is facilitated by attachment means which permit the installer to move the receiving transducer 15 along the inlet line with respect to the transmitting transducer 12 to or from the nodal point of the standing ultrasonic waves that result from conduit resonance. At this point the amplitude of the received signal is maximum.

Figure 4:
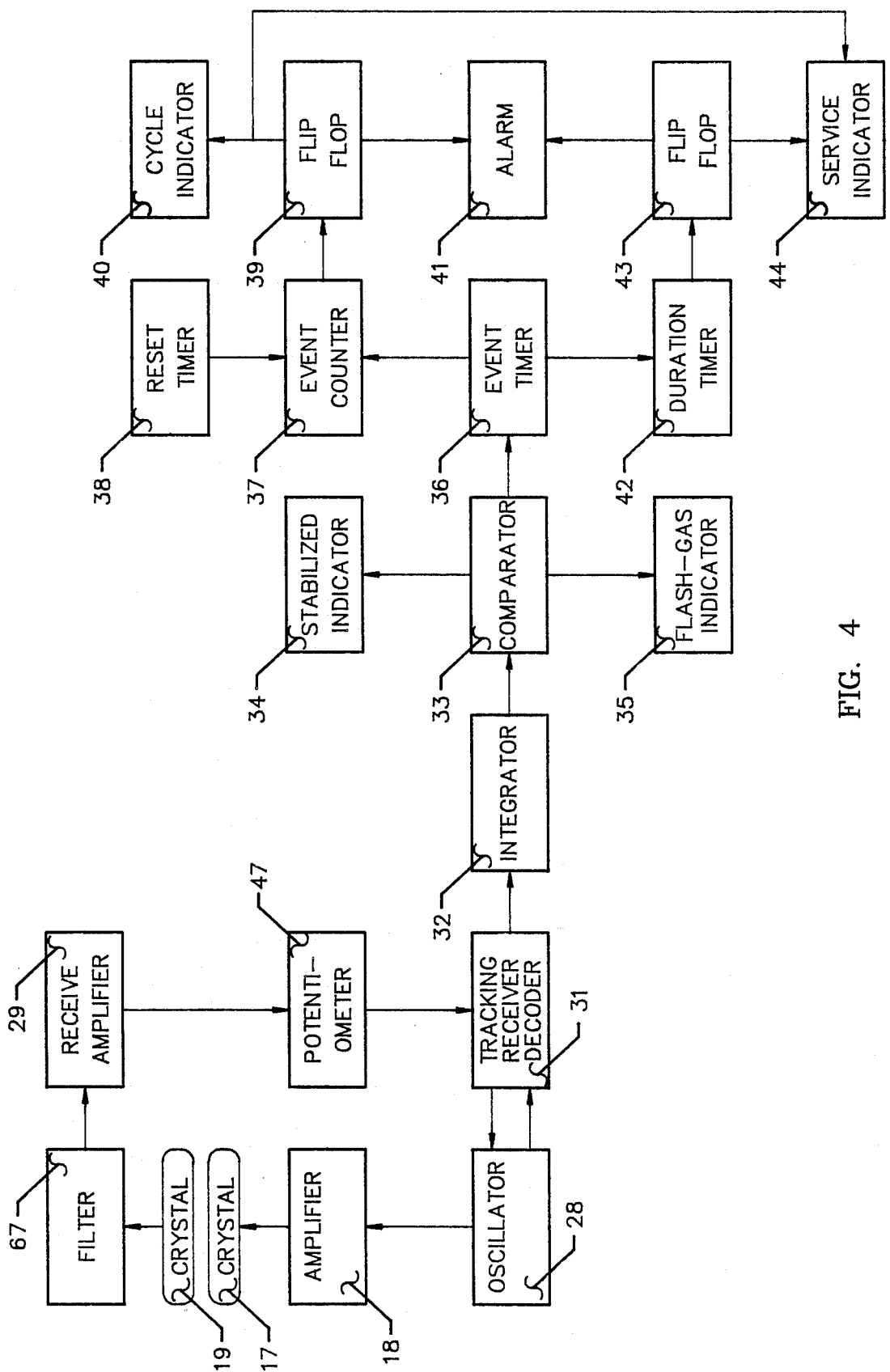
FIG. 4 is a block diagram of the device of the present invention.

Referring now to FIG. 4, the circuit generally comprises commercially available integrated circuits to provide a 44 kHz oscillator 28 and amplifier 18, as the driver to transmit mechanical ultrasonic waves to the conduit 13 of FIG. 1 via the piezo electric Crystal 17. A receiving piezo electric Crystal 19, a Filter 67 and Receive Amplifier 29 receive the output signal generated by crystal 19. A Potentiometer 47 for adjusting receive sensitivity, and a Slaved Tracking Receiver-Decoder 31 which signals the immediate thermodynamic state of the coolant flowing through the inlet line complete the first stage of the circuit.

The signal from the Integrator 32 is conducted to a Comparator 33, a Stabilized Indicator 34 that is activated by the comparator 33 only when the thermodynamic state of the fluid flowing through the inlet line is satisfactory, and a Flash-Gas indicator 35 which is activated by the comparator only when the thermodynamic state of the fluid flowing through the inlet line is not satisfactory.

When the comparator 33 activates the indicator 35 it also signals an Event Timer 36 The event timer determines the time that the indicator 35 is on (times the duration of a single event during which the quality of the refrigerant in the inlet line is not satisfactory).

The event timer is set for one minute and will time significant events (those that occur over a period of one minute or longer). Thus, if the indicator 35 is on for one minute or longer (indicating Flash-Gas within the inlet line for at least one minute), the event timer will signal the event counter 37 to record that event as significant.

A Reset Timer 38 operates to reset the event counter every 30 minutes. Should 7 significant events of one minute or longer be recorded over 30 minutes, the counter will activate the Flip/Flop 39. This flip/flop then turns on and latches a Cycle Indicator 40, a Service Indicator 44, and sounds an alarm 41. If less than 7 significant incidents occur during a 30 minute period, the reset timer resets the event counter which begins to count over again from zero.

The event timer 36 has a second output to a Duration Timer 42 that will time out after 30 minutes. Should a single event of unsatisfactory quality last for 30 minutes, the duration timer circuit will activate a Flip/Flop 43 to turn on the Service Indicator 44 and sound the alarm 41.

Figure 5:
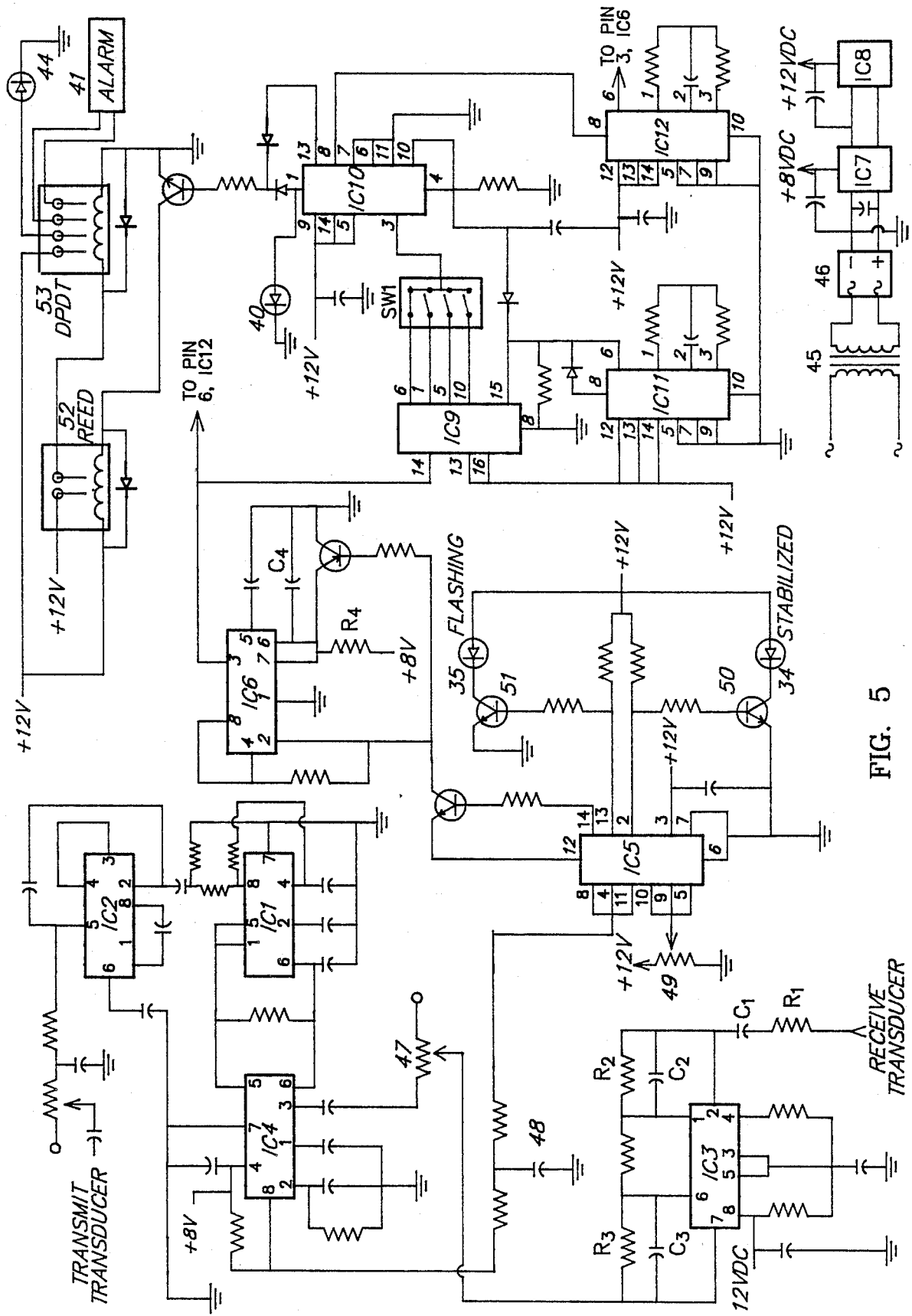
FIG. 5 is a schematic diagram of the monitor circuit.

Referring now to FIG. 5, the specific circuit of the invention is illustrated. The circuit generally comprises twelve commercially available integrated circuits to provide a power supply, an oscillator as the drive to the transmitting transducer a receiver amplifier to receive the electrical signals generated by the receiving transducer, a tracking receiver decoder, integrator and comparator means discussed above, an event timer to verify the duration of episodes and events of inhomogeneity in the fluid flow through the inlet line, an event counter to record the number of significant episodes that occur, a reset timer adjusted to reset the event counter to zero every 30 minutes, and a flip/flop relay that will turn on a cycle indicator and alarm when 7 significant events occur within a 30 minute period.

The monitor circuit may be powered by a 208-230 AC voltage supply from a public utility which is connected to the primary of a transformer 45. The secondary winding of the transformer 45 is arranged to provide a 24 volt AC electrical output to an AC-DC bridge rectifier 46. The integrated circuit IC 7 is a model 7808 precision voltage regulator manufactured by Fairchild to provide a regulated 8 volt output from the power supply. IC 8 is a model 7812 precision voltage regulator, also manufactured by Fairchild, providing a regulated 12 volt DC output.

The oscillator of the monitor comprises the integrated circuits IC 1 and IC 2. IC 1 is a model LM567CP tone decoder/phase-lock loop 8 pin dual in line package (DIP) manufactured by National Semiconductor operated to generate a 44 kHz signal. The 44 kHz signal generated by IC 1 appears on pin 8 thereof and is connected to pin 2 of IC 2. IC 2 is a model LM386 0.7 watt audio amplifier, 8 pin DIP, also manufactured by National Semiconductor to amplify the 44 kHz signal and provide an amplified output signal at pin 5 which is connected to the transmitting transducer 12 of FIG. 1 through conductor 11.

As discussed above, the ultrasonic energy from transducer 12 is transmitted by the conduit 13 to the receiving transducer 15. This transducer converts the received ultrasonic waves into an electrical signal which is transmitted through the conductor 16 to the high pass input filter $R_1 C_1$ of FIG. 5, which attenuates frequencies below about 20 kHz in the signal to pin 2 of IC 3. Resistor $R_2$ and capacitor $C_2$ together with the resistor $R_3$ andcapacitor $C_3$, comprise a low pass filter that attenuates frequencies above about 50 kHz from the signal to pins 1 and 6 of IC 3. The integrated circuit IC 3 is a model LF353 operational amplifier 8 pin DIP manufactured by National Semiconductor. This integrated circuit acts to receive and amplify the electrical signal from transducer 15.

The amplified output from pin 6 of IC 3 is transmitted through a potentiometer 47 to pin 3 of IC 4. In the preferred embodiment, the amplitude of the electrical signal received at pin 3 of IC 4 is set by adjustment of potentiometer 47 to be in the 100-200 millivolt range during normal system operation. IC 4 is a model LM567CP integrated circuit (the same as IC 1). This circuit decodes the 44 kHz signal by converting it into an on/off DC voltage (digital logic signal) at pin 8 of IC 4. The magnitude of the electrical output at pin 8 of IC 4 is a function of the intensity of the mechanical ultrasonic waves received by the transducer 15 and is dependent upon the homogeneity of the refrigerant flowing through the conduit at that instant.

It will be noted that the decoder IC 4 is slaved to the oscillator IC 1 through the interconnection of pins 5 and 6 of both integrated circuits. This forms a unique slaving circuit to avoid frequency drift change between IC 1 and IC 4.

The output of pin 8 of IC 4 is connected to ground through a capacitor 48 which, pursuant to a significant feature of the invention, acts as a time lag circuit to average or integrate any glitches in the receiver amplifier IC 3 and decoder IC 4 circuits. The filtered signal to pins 4, 8, and 11 of IC 5 therefore is an accurate representation of the average quality of the refrigerating medium existing within the inlet line and being monitored.

In the preferred embodiment of this invention, a simple and inexpensive resistor capacitor network is shown as the integrator means. Other known integrator means of averaging the received signal, such as an integrator circuit based upon a microprocessor with appropriate software, is a more sophisticated integrator means to average the signal.

The integrated circuit IC 5 comprises a model LM339 quad comparator, 14 pin DIP manufactured by National Semiconductor. IC 5 operates to compare the averaged DC output from pin 8 of IC 4 to a preset reference voltage determined by voltage divider 49. This preset voltage determines the point at which the comparator (IC 5) is triggered to indicate a flash-gas condition, or a stabilized (normal) condition as compared against the integrated voltage (charge) from the integrator circuit.

The reference voltage is set via a voltage divider 49 connected to pins 5, 9 and 10 of the comparator IC 5. A reference voltage of 5.9 volts DC to pins 5, 9 and 10 was found to be satisfactory as a reference voltage when the input to pin 3 of IC 4 is set between 100 and 200 millivolts durning normal system operation as discussed above. The comparator IC 5 compares the reference voltage supplied to pins 5, 9 and 10 to the varying DC voltage input to pin 8 from the integrator.

During normal operation of the refrigeration system, the voltage at pin 8 of IC 5 will be less than the reference voltage (pin 5 of IC 5). Pin 2 of IC 5 will go positive and operate to drive transistor 50 and energize the light emitting diode 34 indicating normal operation.

When there is a pressure drop in the system that results in significant flashing gas in the liquid flowing through conduit 13, the integrated flashing gas signal received from pin 8 of IC 4 will be greater than the reference voltage input to pin 5 of IC 5, Pin 2 will return to near ground potential and pin 13 of IC 5 will go positive driving transistor 51 to energize light emitting diode 35 and thereby indicate flash-gas within the inlet line of the system, as discussed above.

The comparator IC 5 will also operate to activate a timing sequence by IC 6 (the event timer circuit) simultaneous with the detection of flash-gas within the inlet line.

The event timer, IC 6 is a model LM555 timer manufactured by Fairchild and is used to time the duration of flashing gas within the inlet line (the time that the diode 35 remains on). The timing cycle is determined by the values of $R_4$, $C_4$. We have found that a timing cycle of 1 minute is satisfactory for monitoring the current commercial refrigerants, e.g., R-22 (monochlorodifluoromethane).

During normal operation, when the light emitting diode is on, the event timer is off. The event timer is turned on by an output signal from pin 12 of IC 5 at the same time that the diode 35 is turned on by the output at pin 13 of that circuit. Should the detection of gas bubbles flowing through the inlet line cease prior to time out (prior to 1 minute), the timing sequence of IC 6 will be discontinued and reset by a pulse to pin 2 of IC 6 and not restarted by IC 5 until a subsequent detection of flashing gas.

In the event that the detection of flashing gas within the inlet line continues for longer than the timing cycle of IC 6, (1 minute) IC 6 will time out and pin 3 of IC 6 will go from high to low.

The output of pin 3 of IC 6 is connected to pin 14 of IC 9 which is a model CD4017 CMOS decade counter 16 pin manufactured by RCA used to count the number of significant events of continuous inhomogeneity lasting longer than the 1 minute timing sequence of IC 6. Outputs 10, 1, 5 and 6 from IC 9 are activated by the 4th, 5th, 6th and 7th events longer than 1 minute.

$SW_1$ is a bank of 4 single pole dip switches. The switch from pin 6 is shown closed to connect pin 6 of IC 9 (activated by 7 events), to pin 3 of IC 10.

IC 10 is a model CD4013 CMOS dual "D" flip/flop DIP manufactured by RCA. One half of IC 10 (Flip/Flop 1) is utilized to latch a logic high output when the counter IC 9 reaches a predetermined number of recorded events of inhomogeneity lasting more than 1 minute. When IC 10 reaches a count of 7, a latched logic high output from pin 1 thereof (Flip/Flop 1) drives light emitting diode 401 to indicate the excessive number of significant events of inhomogeneity (7), lasting 1 minute or longer.

A reset timer, IC 11, which comprises a model CD 4541 CMOS oscillator-timer, 14 pin DIP manufactured by RCA, is used to reset the event counter IC 9 to zero after a predetermined period of time, for example, one half hour. A reset timer, IC 11, which comprises a model CD 4541 CMOS oscillator-timer, 14 pin DIP manufactured by RCA, is used to reset the event counter IC 9 to zero after a predetermined period of time, for example, one half hour.

A duration counter is included in the monitor circuit to signal the operator when a significant event (flashgas) at the inlet line), exceeds 30 minutes. The duration timer, IC 12, is a model CD4541 CMOS oscillator timer 14 pin DIP manufactured by RCA. This integrated circuit is activated at pin 6 by the low logic signal at pin of IC 6 when a significant event occurs (lasting 1 minute). The low logic signal at pin 3 of IC 6 is conducted both to pin 6 of the duration timer circuit and to pin 14 of the counter circuit IC 9 simultaneously. Reversal of the high low signal at pin 6 of IC 12 (due to a return to normal operation of the refrigeration system), resets the 30 minute timing cycle to zero. If the logic low signal at pin 12 of IC 12 continues for 30 minutes, IC 12 times out and pin 8 of IC 12 goes positive.

The signal from pin 8 of IC 12 is conducted to pin 8 of the second half of IC 10 (Flip/Flop 2), and latches a logic signal high at pin 13 of IC 10 closing a reed relay 52 and turning on the double pole double throw relay to activate the light emitting diode 44 and the alarm circuit.

It will be noted that the output from pin 1 of IC 10 to the cycle indicator (diode 40), will also turn on the service indicator. Thus the operator will know, if the cycle indicator is not on, that the malfunction was one of 30 minutes duration.

The present invention, therefore, provides a highly advantageous device for continuously monitoring a fluid flow in the inlet line of a refrigeration system. The device automatically detects the flow of impurities and ascertains valuable information on the duration of impurity flow and the number of significant events of impurity flow. An operator is fully appraised of the condition of system operation by simple observation of the indicating elements on the front panel of the monitoring device.

In summation, the invention detects and indicates the presence of impurities in the inlet line, verifies the occurrence of impurity flow for a significant continuous period of time and records and indicates an unacceptable number of significant events of continuous impurity flow within a fixed period of system operation. Such information on system operation readily affords a continuous and comprehensive monitoring of proper operation.

It should be understood, of course, that the specific form of the invention herein illustrated and described is intended to be representative only, as certain changes may be made therein without departing from the clear teachings of the disclosure. Accordingly, reference should be made to the following appended claims in determining the full scope of the invention.

What is claimed is:

1. A device useful for monitoring the thermodynamic state of a fluid flowing through a conduit, which comprises:
   (a) a first electromechanical transducer,
   (b) means to acoustically couple said first transducer to a conduit,
   (c) a precision oscillator which provides a driving electrical signal characterized by an ultrasonic frequency to said first transducer,
   (d) a second electromechanical transducer,
   (e) means to acoustically couple said second transducer to said conduit in a spaced relationship to said first transducer,
   (f) a receive amplifier tuned to the output frequency of said oscillator operating to receive and amplify the ultrasonic signal received from said second transducer,
   (g) a tracking receiver-decoder operating to convert the ultrasonic signal received from said receive amplifier into a digital logic signal,
   (h) an integrator circuit operating to average said digital logic signal from said tracking receiver-decoder, and
   (i) a comparator connected to the output of said integrator operating to compare the averaged DC output from said integrator with a preset reference voltage and to provide first and second signals indicative of said comparison.

2. The device of claim 1 wherein said first and second signals are visual.

3. The device of claim 2 wherein said first and second signals activate first and second light emitting diodes.

4. The device of claim 1 wherein said first signal is provided by the comparator when the output from the integrator is less than the preset reference voltage and said second signal is provided by the comparator when the output from the integrator is greater than the preset reference voltage.

5. The device of claim 1 wherein said precision oscillator is slaved to said tracking receiver-decoder whereby any change in the frequency received by said tracking receiver-decoder results in an identical change in the ultrasonic frequency of the oscillator.

6. The device of claim 1 wherein means is provided to adjust the sensitivity of said tracking receiver-decoder.

7. The device of claim 1 wherein an event timer circuit is provided to verify the duration of one of said first and second signals provided by said comparator.

8. The device of claim 7 wherein said event timer circuit will verify a signal lasting one minute or longer.

9. The device of claim 8 characterized by an event counter which functions to detect and count the number of signals lasting one minute or longer.

10. The device of claim 1 wherein one or said first and second signals from said comparator is conducted to a duration timer circuit which operates to trigger an alarm when that signal provided by said comparator continues for about 30 minutes.

11. The device of claim 1 wherein said tracking receiver-decoder is slaved to said precision oscillator whereby any change in the ultrasonic frequency of the oscillator results in an identical change in the frequency received by the tracking receiver-decoder.

12. In a device for determining the quality of a refrigerant flowing through a rigid conduit by measuring the transmission of ultrasonic waves through the conduit-refrigerant medium, the improvement which comprises, slaving an analog to digital tracking receiver-decoder circuit and an oscillator circuit whereby any drift in the frequency received by the tracking receiver-decoder is compensated for by a corresponding change in oscillator frequency and any drift in the oscillator frequency is compensated for by a corresponding change in the frequency received by the tracking receiver-decoder.

13. In a device for determining the quality of a refrigerant flowing through a rigid conduit by measuring the transmission of ultrasonic waves through the conduit-refrigerant medium, the improvement which comprises, an integrator circuit which functions to average the output from a tracking receiver-decoder circuit.

14. A process for detecting inhomogeneities in a refrigerant flowing through a conduit, which comprises the steps of:
(a) generating mechanical ultrasonic wave energy,
(b) transmitting said mechanical wave energy from a first point through said refrigerant and said conduit,
(c) receiving said mechanical wave energy at a second point spaced from said first point,
(d) converting said received mechanical wave energy into an analog electrical signal.
(e) converting the analog electrical signal into a digital logic signal,
(f) averaging said digital logic signal, and
(g) analyzing the averaged digital logic signal to detect changes in the logic signal caused by inhomogeneity in the fluid flow, timing the duration of detected changes in said averaged logic signal and recording events of detected changes having a time duration of more than a predetermined amount.

15. The process of claim 14 wherein said second point at which said mechanical wave energy is received is moved with respect to said first point to a different point at which the said analog electrical signal is maximum.

16. The process of claim 14 wherein the averaged digital logic signal is adjusted to provide a visual indication when the quality said refrigerant is satisfactory.

17. The process of claim 16 wherein adjustment of the averaged logic signal is made by means of a potentiometer.

18. A process for detecting inhomogeneities in a refrigerant flowing through a conduit, which comprises the steps of:
(a) generating ultrasonic mechanical wave energy,
(b) transmitting said generated mechanical wave energy from a first point through said refrigerant and said conduit.
(c) receiving said mechanical wave energy at a second point spaced from said first point,
(d) converting said received mechanical wave energy into an analog electrical signal,
(e) converting said analog electrical signal into a digital logic signal,
(f) averaging the digital logic signal, and
(g) analyzing the averaged digital logic signal to detect changes in said averaged signal caused by inhomogeneities in the fluid flow, timing the duration of detected changes in said averaged signal and sounding an alarm when the detected change of said averaged signal has a time duration of more than about 30 minutes.

19. The process of claim 18 wherein said second point at which said mechanical wave energy is received is moved with respect to said first point to a different point at which the said analog electrical signal is maximum.

20. The process of claim 18 wherein the averaged digital logic signal is adjusted to provide a visual indication when the quality of said refrigerant is satisfactory.

* * * * *